United States Patent [19]

Smithwick, Jr.

[11] 3,956,219

[45] May 11, 1976

[54] CROSSLINKED POLYSTYRENE AND SUBSTITUTED POLYSTYRENE COMPOSITIONS

[75] Inventor: Edward L. Smithwick, Jr., Indianapolis, Ind.

[73] Assignee: Eli Lilly and Company, Indianapolis, Ind.

[22] Filed: Oct. 11, 1974

[21] Appl. No.: 514,165

Related U.S. Application Data

[63] Continuation-in-part of Ser. No. 328,551, Feb. 1, 1973, Pat. No. 3,857,829.

[52] U.S. Cl. .......................... 260/30.2; 260/30.4 R; 260/33.6 UA; 260/33.8 UA; 260/112.5 R
[51] Int. Cl.² ..................... C08K 5/01; C08K 5/02; C08K 5/14; C08K 5/34
[58] Field of Search ... 260/30.2, 33.6 UA, 33.8 UA, 260/30.4 R, 112.5

[56] References Cited
UNITED STATES PATENTS

| | | | |
|---|---|---|---|
| 3,714,140 | 1/1973 | Sipos | 260/112.5 |
| 3,764,384 | 10/1973 | Berni | 260/30.2 |

FOREIGN PATENTS OR APPLICATIONS

| | | | |
|---|---|---|---|
| 967,051 | 8/1964 | United Kingdom | 260/34.2 |

*Primary Examiner*—Allan Lieberman
*Attorney, Agent, or Firm*—William E. Maycock; Everet F. Smith

[57] ABSTRACT

A composition which is either polystyrene or a substituted polystyrene crosslinked with divinylbenzene and swollen by N-methyl-2-pyrrolidone, which composition is useful in purifying blocked synthetic peptides by means of gel exclusion chromatography and in solid-phase peptide synthesis.

7 Claims, No Drawings

CROSSLINKED POLYSTYRENE AND SUBSTITUTED POLYSTYRENE COMPOSITIONS

CROSS-REFERENCE TO RELATED APPLICATION

This application is a continuation-in-part of copending application Ser. No. 328,551, filed Feb. 1, 1973 now U.S. Pat. No. 3,857,829.

BACKGROUND OF THE INVENTION

This invention relates to a composition which is either polystyrene or a substituted polystyrene crosslinked with divinylbenzene and swollen by N-methyl-2-pyrrolidone.

Briefly, peptides are polyamides comprising two or more amino acids. Synthetic peptides generally are prepared by well-established procedures which require the blocking of various reactive groups in order to minimize degradation and side reactions. The blocking groups then are removed as a last step in the synthetic procedure, with purification procedures normally being carried out prior to deblocking.

Peptide synthesis usually involves fragment condensation methods which can be summarized as follows. A plurality of amino acid residues are condensed via peptide linkages to give a fragment, A-COOH, terminating in a carboxylic acid group and wherein all other reactive groups are blocked. Similarly, an amine-terminated fragment, H$_2$N—B, is prepared. The two fragments then are combined to give A—CONH—B, which in turn can be used as an intermediate to prepare a higher molecular weight peptide or deblocked and used per se.

Blocked peptides consisting of more than about four amino acids usually are insoluble in most solvents, water included. Such blocked peptides are, however, soluble in the high-solvency liquids which include N,N-dimethylformamide (DMF), N,N-dimethylacetamide (DMAC), dimethylsulfoxide (DMSO), hexamethylphosphoric triamide (HMPA), and the like. But blocked peptides are difficult to purify by crystallization because the blocked peptide fragments, A—COOH and H$_2$N—B, and the final product prepared therefrom, A—CONH—B, have similar solubilities, a problem not eliminated by deblocking.

Fortunately, blocked peptides can be purified by chromatographic techniques. Ideally, such techniques will be passive, as contrasted with, for example, ion exchange chromatography. However, typical prior art passive procedures, such as adsorption chromatography utilizing DMF as solvent and a hydrophilic, insoluble, crosslinked dextran as the resin, generally are satisfactory only for blocked peptides having fewer than about eight amino acid residues.

Theoretically, gel exclusion chromatography (synonymous with gel filtration and gel permeation chromatography) is an ideal system for the separation of blocked peptides. However, most solvents suitable for swelling the resin, which solvents include, among others, benzene, toluene, and tetrahydrofuran (THF), are poor solvents for blocked peptides.

It will be recognized by those skilled in the art that gel exclusion chromatography requires that the resin be swollen by the solvent, for it is this swelling which produces the voids by means of which the separation of blocked peptides occurs. Furthermore, increasing the degree of swelling generally increases resolution, a term employed herein to mean separation of the final blocked peptide from the blocked peptide fragments or intermediates. Hence, the problem heretofore has been the lack of a good blocked peptide solvent which also is capable of adequately swelling a suitable resin, which resin usually is polystyrene crosslinked with divinylbenzene. In the typical prior art procedures mentioned hereinbefore, there is only minimal swelling of the resin by the solvent.

Resin swelling also is important in the recently developed procedure known as solid-phase peptide synthesis. Solid-phase peptide synthesis is based upon the premise that amino acids can be assembled into a peptide chain of any desired sequence while one end of such chain is anchored to an insoluble support. Most commonly, the insoluble support is a substituted polystyrene crosslinked with divinylbenzene, wherein the polystyrene is substituted with an appropriate anchoring group, i.e., a group capable of reacting with the amino or carboxy terminus of an amino acid or peptide to give a covalent bond.

The potentially reactive anchoring group remains unreactive when in a nonsolvated state. The role of swelling of the insoluble support becomes more fully appreciated upon recognition of the general resemblance between swollen and dissolved states. Indeed, swelling is a process of incipient dissolution of segments between crosslink sites within the polymer network. Thus, the success of solid-phase procedures is to a large extent dependent upon the appropriate solvation of the anchoring group loci.

Under ideal solvation or swelling conditions, both the nonpolar, substituted polystyrene support and the more polar peptide chains are in an essentially extended configuration, thereby permitting ready access by reagents. In the nonpolar solvents commonly employed, such as methylene chloride, the substituted polystyrene is extended, while the peptide chains are not. The reverse situation occurs in the presence of polar solvents, such as acetic acid, DMF, alcohols, and the like. Thus, ideal swelling conditions have not heretofore been attainable.

SUMMARY OF THE INVENTION

It is an object of the present invention to provide a composition which is suitable for purifying blocked synthetic peptides by means of gel exclusion chromatography.

A further object of the present invention is to provide a composition which is well-suited for use in solid-phase peptide synthesis.

These and other objects will be readily apparent to those skilled in the art from a consideration of the specification and claims which follow.

It unexpectedly has been discovered that either polystyrene or a substituted polystyrene crosslinked with from about 0.5 to about 3 percent by weight divinylbenzene is swollen to an equilibrium state by a solvent which consists essentially of N-methyl-2-pyrrolidone (NMP). The swelling action of NMP on such crosslinked polystyrene or substituted polystyrene was unexpected since other high-solvency liquids, such as DMF, DMAC, and DMSO, are good peptide solvents but have only a minimal swelling effect on such crosslinked polystyrene or substituted polystyrene.

The resulting composition, i.e., crosslinked polystyrene or substituted polystyrene swollen by NMP, which constitutes the present invention, is useful in the separation of blocked peptides having molecular weights below about 11,000 by means of gel exclusion chromatography, or in the synthesis of such peptides by means of solid-phase procedures. Many such blocked peptides when unblocked are biologically active and therapeutically important. Others can be used as intermediates to prepare higher molecular weight peptides which are biologically active and therapeutically important.

Hormones constitute an important class of such biologically active and therapeutically important peptides. Examples of useful hormones include, among others, oxytocin, the principal uterine-contracting and lactation-stimulating hormone; vasopressin, which is used as an antidiuretic; luteinizing hormone releasing hormone (LH—RH), useful in stimulating fertility in humans and synchronizing estrous in farm animals; insulin, which is used in the treatment of diabetes mellitus; and glucagon, useful in the emergency treatment of severe hypoglycemic reactions in diabetic patients receiving insulin and in psychiatric patients during insulin shock therapy.

Another class of biologically active and therapeutically important peptides consists of vasoactive agents, such as angiotensin II 5-isoleucine, angiotensin II 5-valine, and angiotensin II amide 5-valine, which materials are vasoconstrictor, vasopressor agents.

Still another class of such biologically active and therapeutically important peptides consists of antibiotics, such as gramicidin S.

DETAILED DESCRIPTION OF THE INVENTION

As indicated hereinabove, the present invention discloses a composition which comprises a resin crosslinked with from about 0.5 to about 3 percent by weight divinylbenzene and swollen to an equilibrium state by a solvent which is essentially N-methyl-2-pyrrolidone, which resin is polystyrene or a polystyrene substituted with an anchoring group capable of reacting with the amino or carboxy terminus of an amino acid or peptide to give a convalent bond.

The term "substituted polystyrene" as used herein is interchangeable with such phrases as "polystyrene substituted with an anchoring group" and is meant to include polystyrene substituted with appropriate anchoring groups and, optionally, other groups such as chloro, bromo, nitro, and the like. Examples of suitable anchoring groups include, among others, chloromethyl, bromomethyl, hydroxymethyl, $\beta$-hydroxyethylsulfonylmethyl, N-acetyl-N-($\beta$-hydroxyethyl)aminomethyl, $\gamma$-hydroxybutyryl, chloroacetyl, chlorocarbonyloxymethyl, chlorosulfonyl, and the like. Such substituted polystyrenes are either commercially available or prepared by known methods; see, for example, R. B. Merrifield in "Advances in Enzymology," Vol 32, F. F. Nord, Ed., Interscience Publishers, New York, 1969, pp. 221 ff., and references cited therein. It will be apparent to those skilled in the art that, in general, polystyrene will be utilized when a composition of the present invention is to be employed in gel exclusion chromatography. On the other hand, a polystyrene substituted as described above will be utilized when such composition is to be employed in solid-phase peptide synthesis.

For brevity, the discussion which follows is directed primarily to the use of crosslinked polystyrene swollen by NMP in gel exclusion chromatography. However, the principles involved in such discussion apply equally to the use in solid-phase peptide synthesis of a crosslinked substituted polystyrene swollen by NMP.

As indicated hereinbefore, the requisite separation of blocked peptide product A—CONH—B from other materials is readily accomplished by means of gel exclusion chromatography wherein a composition of the present invention is utilized as the chromatographic medium. To obtain complete separation, it is preferred that the molecular weight of A—CONH—B be at least twice that of the highest molecular weight fragment employed in the preparation of A—CONH—B. However, separation generally can be improved by reducing the degree of divinylbenzene crosslinking in the resin. Understandably, optimum conditions for the purification of any given blocked peptide will vary from case to case and can be determined readily by one of ordinary skill in the art.

The degree of divinylbenzene crosslinking in the polystyrene resin employed can range from about 0.5 percent to about 3 percent by weight. Preferably, the degree of divinylbenzene crosslinking will be no more than about 2 percent, with 1 percent by weight being most preferred. A satisfactory chromatographic medium is obtained by equilibrating the resin with solvent to obtain maximum swelling which will remain essentially constant during the separation process.

As stated hereinbefore, swelling of the resin by the solvent is an essential feature of gel exclusion chromatography. Since the size of the voids in the chromatographic medium is directly proportional to the degree of swelling, increasing the degree of swelling increases the maximum molecular weight of blocked peptide molecules which can penetrate the chromatographic medium.

From the foregoing, it is apparent that resolution of any given blocked peptide is a function of the degree of swelling of the chromatographic medium. The degree of swelling in turn is a function of both the solvent or solvent mixture employed and the degree of divinylbenzene crosslinking. These basic principles are illustrated by the data in Tables I and II.

The data in Tables I and II were obtained by thoroughly shaking at ambient temperature 1.0 gram of 200–400 mesh polystyrene crosslinked with either 1 or 2 percent divinylbenzene with an excess volume of solvent and allowing the mixture to settle for 24 hours. The volume of the polystyrene was recorded either directly or as a percent increase in volume compared to the volume of the resin is DMF.

Table I

| Swelling of polystyrene crosslinked with 1 percent divinylbenzene in NMP-DMF solvent mixtures. | |
|---|---|
| Percent NMP in DMF | Percent Increase over DMF |
| 0 | — |
| 20 | 14 |
| 40 | 26 |
| 60 | 36 |
| 80 | 45 |
| 100 | 54 |

Table II

Swelling of polystyrene crosslinked with divinylbenzene in various solvents

| Solvent | 2 Percent Divinylbenzene | | | 1 Percent Divinylbenzene | | | |
|---|---|---|---|---|---|---|---|
| | Vol., ml. | % Inc.[b] | % Max.[c] | Vol., ml. | % Inc. 2%[d] | % Inc.[b] | % Max.[c] |
| DMF | 3.7 | — | 0 | 5.0 | 35 | — | 0 |
| EtOAC[a] | 3.8 | 4 | 8 | 5.2 | 35 | 4 | 6 |
| THF | 5.5 | 49 | 92 | 8.5 | 55 | 70 | 97 |
| NMP | 5.3 | 43 | 81 | 7.7 | 45 | 54 | 75 |
| Benzene | 5.6 | 53 | — | 8.6 | 52 | 72 | — |

[a] Ethyl acetate
[b] Increase in resin volume expressed as a percent volume increase over the volume of the resin in DMF.
[c] Increase in resin volume expressed as a percentage of the maximum resin volume obtainable and resulting from the use of benzene as solvent.
[d] Increase in resin volume expressed as a percent increase over the resin volume obtained with the same solvent and 2% divinylbenzene.

From Table I it is seen that the degree of swelling increases as the proportion of NMP in the solvent mixture is increased. Clearly, the degree of swelling of the resin can be controlled by varying solvent composition.

An examination of Table II leads to the following conclusions:

1. Reducing the degree of divinylbenzene crosslinking permits every solvent tested to at least partially swell polystyrene.
2. Of the solvents employed, benzene results in the greatest degree of swelling of polystyrene.
3. Every solvent tested swells polystyrene to a greater degree as the degree of divinylbenzene crosslinking decreases.

The degree of swelling of a crosslinked substituted polystyrene parallels the swelling of crosslinked polystyrene as discussed hereinbefore. Furthermore, such degree of swelling of a cross-linked substituted polystyrene remains relatively unaltered upon attaching an amino acid or peptide to the crosslinked substituted polystyrene. These principles are illustrated by the data in Table III.

The data in Table III were obtained as described for Table II, except that the resin was either chloromethyl-substituted polystyrene crosslinked with 1 percent divinylbenzene and containing 0.75 mmole chlorine per gram of resin or such resin reacted with t-butyloxycarbonylleucine and containing 0.522 mmole blocked amino acid per gram of resin.

course, this determination cannot be considered to be absolute since the sizes of the voids in the swollen polystyrene are not uniform and vary over quite a wide range. It does, however, serve as a useful approximation.

It should be apparent to those skilled in the art that it is possible to purify blocked synthetic peptides having molecular weights above about 11,000, provided certain limitations are met. First, such peptides must be soluble in NMP. Furthermore, at least one of the fragments used to prepare such peptides must have a molecular weight below about 11,000; i.e., at least one fragment must have significant interaction with the chromatographic medium. Without such interaction, all of the fragments and the product must simply flow through the column without any separation of any kind taking place. However, by employing in excess the fragment which has significant interaction with the chromatographic medium, only that fragment and the product will be present to any significant extent at the conclusion of the coupling reaction. Upon chromatographing such a mixture, the product should pass through the column unhindered. The fragment, however, should be delayed to an extent sufficient to permit resolution of the product.

Of course, the technique of using one blocked peptide fragment in excess advantageously can be employed even if all peptides involved have molecular weights below about 11,000. For example, suppose that Table III Swelling in various solvents of chloromethyl-substituted polystyrene crosslinked with divinylbenzene, before and after reacting with t-butyloxycarbonylleucine.

| Solvent | Cl-CH$_2$-Resin | | | BOC-Leu-O-CH$_2$-Resin | | | |
|---|---|---|---|---|---|---|---|
| | Vol., ml. | % Inc.[b] | % Benz.[c] | Vol., ml. | % Change[d] | % Inc.[b] | % Benz.[c] |
| DMF | 6.2 | — | 0 | 5.2 | −16 | — | 0 |
| EtOAC[a] | 5.5 | −11 | — | 5.6 | 2 | 8 | 15 |
| THF | 8.5 | 37 | 115 | 7.8 | −8 | 50 | 96 |
| NMP | 8.0 | 29 | 90 | 7.1 | −11 | 37 | 70 |
| Benzene | 8.2 | 32 | — | 7.9 | −4 | 52 | — |

[a] Ethyl acetate.
[b] Increase in resin volume expressed as a percent volume increase over the volume of resin in DMF.
[c] Increase in resin volume expressed as a percentage of resin volume obtainable from the use of benzene as solvent.
[d] Change in resin volume expressed as a percent increase or decrease over the volume of Cl-CH$_2$-Resin in the same solvent.

It is known that with benzene and polystyrene crosslinked with 1 percent divinylbenzene, molecules having molecular weights above about 14,000 are excluded from the voids of the polystyrene. This fact coupled with the data in Tables I and II leads to the conclusion that the use of NMP and polystyrene crosslinked with 1 divinylbenzene would exclude from the voids of the polystyrene molecules having molecular weights above about 11,000 (which is about 75 percent of 14,000). Of a dipeptide and an octapeptide (both suitably blocked) are to be combined to give a blocked decapeptide. Employing the dipeptide in excess will practically eliminate the octapeptide which normally cannot be completely separated from the decapeptide in one pass. Of course, it should be possible to separate an octapeptide from a decapeptide if multiple passes and greatly reduced yield of decapeptide are acceptable. Clearly, however, it is most advantageous if a single pass can be employed.

As stated hereinbefore, the present invention requires the use of NMP as solvent, although up to about 5 percent by volume of cosolvents, such as chloroform, methylene chloride, 1,2-dichloroethane, tetrahydrofuran, benzene, toluene, and the like, can be tolerated, provided that such cosolvents swell the crosslinked polystyrene to a degree which is about equal to or greater than the degree of swelling of such crosslinked polystyrene which results from NMP. Consequently, the NMP must be essentially anhydrous since water does not swell such crosslinked polystyrene. Because mixtures of polar solvents, chloroform, and large blocked peptides tend to result in the formation of blocked peptide chloroform solvates, chloroform is a preferred cosolvent; the preferred level of use of this cosolvent is 2 percent by volume. However, unless chloroform is required to aid in solubilizing large blocked peptides, the use of such cosolvent is not preferred.

In the use of a composition of the present invention in gel exclusion chromatography, standard chromatographic techniques are employed. The resin is equilibrated with NMP. The resulting slurry then is transferred to a suitable glass column and allowed to pack by gravity while maintaining a flow condition. The resulting bed is washed with NMP to remove soluble polymeric materials. The mixture to be separated, as an NMP solution, is added to the column and eluted with NMP. Usually, constant volume fractions are collected and combined as necessary.

The course of elution can be followed by any of the various known methods, such as the biuret test, refractive index, ultraviolet absorption above about 290 m$\mu$, and optical rotation, among others. A particularly useful method which is preferred is to employ blocking groups which impart color to the blocked peptide so that the course of elution can be followed visually.

Column capacity, defined herein as the maximum amount of blocked peptides which can be separated with a given amount of resin, is dependent upon the physical nature of the chromatographic medium, the molecular weights of the blocked peptides involved, and other factors. As a general rule, however, a 165 × 2.5 cm. column of 200–400 mesh divinylbenzenecrosslinked polystyrene has a capacity of about 200 mg. of blocked peptide.

In the following examples which illustrate the use of a composition of the present invention in gel exclusion chromatography, all percentages and parts are by weight unless otherwise specified. Unless otherwise specified, the chromatographic medium is 200–400 mesh and the NMP is both distilled and anhydrous. In every instance both the column and the solvent reservoir are protected from moisture by means of drying tubes.

EXAMPLE 1

Column Preparation

Polystyrene crosslinked with 2 percent divinylbenzene is equilibrated with NMP for 18 hours. The resulting slurry is transferred to a 2.5-cm. glass column and allowed to pack by gravity while being maintained in a flow condition; final bed depth is 165 cm. The bed is washed thoroughly with NMP until the effluent is free of soluble polymeric material.

Separation of Blocked Tripeptide from Blocked Amino Acid

To the above-described column is applied a mixture of 0.1 part of t-butyloxycarbonylmethionyl-asparaginyl-O-benzylthreonine 4-(4-methoxyphenylazo)benzyl ester and 0.1 part of t-butyloxycarbonylglycine 4-(4-methoxyphenylazo)benzyl ester in 2.0 parts of NMP. The column is eluted with NMP and 6-ml. fractions collected. The course of elution is followed visually since the 4-(4-methoxyphenylazo)benzyl blocking group is yellow in color, which color is imparted to each component blocked therewith. Fractions 60–66, inclusive, are combined and diluted with distilled water. The resulting yellow precipitate is collected by centrifugation and dried in vacuo to give 0.08 part of material having the required amino acid analysis for the tripeptide (amino acid content, in $\mu$moles/mg.: methionine, 0.80; asparagine, as aspartic acid, 0.859; and threonine, 0.827). In a similar manner, 0.08 part of material containing only glycine is isolated from fractions 77–85, inclusive (amino acid content, in $\mu$moles/mg.: glycine, 5.96).

The blocked tripeptide is prepared by treating t-butyloxycarbonylmethionyl-asparaginyl-O-benzylthreonine in N,N-dimethylformanide with 4-(4-methoxyphenylazo)benzyl bromide in the presence of dicyclohexylamine. The blocked amino acid is prepared by treating t-butyloxycarbonylglycine with 4-(4-methoxyphenylazo)benzyl alcohol in anhydrous pyridine. 4-(4-Methoxyphenylazo)benzyl bromide is obtained by treating the corresponding alcohol with hydrogen bromide in acetic acid, as known to those skilled in the art. The alcohol can be prepared according to the procedure of R. Schwyzer et al., *Helv. Chim. Acta*, 41, 491 (1958).

EXAMPLE 2

Separation of Blocked Octapeptide from Blocked Tripeptide

To a column essentially the same as that described in Example 1 is applied a mixture of 0.1 part of t-butyloxycarbonylphenylalanyl-valyl-glutaminyl-phenylalanyl-leucylmethionyl-asparaginyl-O-benzylthreonine 4-(4-methoxyphenylazo)benzyl ester and 0.1 part of t-butyloxycarbonylmethionylasparaginyl-O-benzylthreonine 4-(4-methoxyphenylazo)benzyl ester in 4.0 parts of NMP. The column is eluted with NMP as described in Example 1. A yellow solid, 0.03 part, is isolated from fractions 45–49, inclusive, as described in Example 1 and has the required amino acid composition for octapeptide (amino acid content, in $\mu$moles/ml.: phenylanalanine, 134; valine, 0.700; glutamine, as glutamic acid, 0.729; leucine, 0.700; methionine, 0.564; asparagine, as aspartic acid, 0.734; and threonine, 9.690). In a similar manner, 0.09 part of material having the required amino acid analysis for tripeptide is isolated from fractions 56–61, inclusive (amino acid content, in $\mu$moles/ml.: methionine, 1.12; asparagine, as aspartic acid, 1.36; and threonine, 1.26).

The blocked tripeptide is the blocked tripeptide of Example 1. The blocked octapeptide is prepared by coupling the blocked tripeptide with the appropriate blocked pentapeptide, using techniques well known to those skilled in the art. The low recovery of blocked octapeptide results from unavoidable handling losses resulting from both the small quantities involved and the physical state of the recovered octapeptide.

EXAMPLE 3

Separation of Blocked Tetradecapeptide from Blocked Octapeptide

A chromatography column is prepared as described in Example 1, except that the resin is polystyrene crosslinked with 1% divinylbenzene. To the column is applied a mixture of 0.25 part of crude t-butyloxycarbonyl-O-benzylseryl-G-nitroarginyl-G-nitroarginyl-alanyl-glutaminyl-$\beta$-cyclopentylasparatyl-phenylalanyl-valyl-glutaminyl-phenylalanyl-leucylmethionyl-asparaginyl-O-benzylthreonine 4-(4-methoxyphenylazo)benzyl ester and 0.025 part of phenylalanyl-valyl-glutaminyl-phenylalanyl-leucyl-methionyl-asparaginyl-O-benzylthreonine 4-(4-methoxyphenylazo)benzyl ester in 1 part of NMP. The column is eluted as described in Example 1. From combined fractions 61–66, inclusive, is isolated as described in Example 1, 0.002 part of yellow solid having the required amino acid analysis for tetradecapeptide (amino acid content, in $\mu$moles/mg.:serine, 0.239; arginine, 0.437; alanine, 0.233; glutamine, 0.473; aspartic acid, 0.222; asparagine, as aspartic acid, 0.222; phenylalanine, 0.433; valine, 0.232; leucine, 0.227; methionine, 0.035, plus methionine sulfoxide and methionine sulfone; and threonine, 0.216). In a similar manner, 0.020 part of material having the required amino acid analysis for octapeptide is isolated from combined fractions 77–86, inclusive (amino acid content, in $\mu$moles/mg.: phenylalanine, 0.736; valine, 0.318; glutamine, 0.386; leucine, 0.402; methionine, 0.361; asparagine, as aspartic acid, 0.441; and threonine, 0.500).

The blocked octapeptide is the blocked octapeptide of Example 2. The blocked tetradecapeptide is prepared by coupling the blocked octapeptide with the appropriate blocked hexapeptide, using techniques well known to those skilled in the art.

EXAMPLE 4

Preparation of Active Tetracosapeptide Fragment of Adrenocorticotropic Hormone (ACTH)

Following known procedures, a hexapeptide and an octapeptide are coupled by converting the hydrazide group of the hexapeptide to the corresponding azide with nitrous acid, followed by treatment with triethylamine. The hexapeptide is $N_\alpha$-benzyloxycarbonyl-$N_\epsilon$-t-butyloxycarbonyllysyl-prolyl-valylglycyl-$N_\epsilon$-t-butyloxycarbonyllysyl-$N_\epsilon$-t-butyloxycarbonyllysine hydrazide and the octapeptide is arginyl-arginyl-prolyl-valyl-$N_\epsilon$-t-butyloxycarbonyllysyl-valyl-tyrosyl-proline dihydrochloride t-butyl ester. The crude tetradecapeptide thus obtained is isolated as a solid, dissolved in NMP, and chromatographed as described in Example 3.

The purified tetradecapeptide obtained above is treated in solution with hydrogen at atmospheric pressure in the presence of 5 percent palladium on carbon in order to remove the benzyloxycarbonyl blocking group from the terminal lysyl residue. The hydrogenolysis product then is reacted with the decapeptide, t-butyloxycarbonylseryl-tyrosyl-serylmethionyl-o-t-butylglutamyl-histidyl-phenylalanyl-arginyltrypotophyl-glycine hydrochloride, in the presence of N,N'-dicyclohexylcarbodiimide. The resulting blocked tetracosapeptide is chromatographed as described above and the purified peptide deblocked by treating with trifluoroacetic acid to give pure adrenocorticotropic hormone tetradecapeptide fragment.

EXAMPLE 5

Preparation of Insulin B Chain

A hexapeptide, benzyloxycarbonylleucyl-tyrosyleucyl-valyl-S-benzylcysteinyl-glycine hydrazide and a decapeptide, glutamyl-($\gamma$-t-butyl ester)-$N_\epsilon$-tosylarginyl-glycyl-phenylalanyl-phenylalanyl-tyrosyl-threonyl-prolyl-$N_\epsilon$-tosyllysyl-alanine methyl ester, are coupled by means of the nitrous acid procedure described in Example 4. The resulting hexadecapeptide is chromatographed and subjected to hydrogenolysis as described in Example 4. The above-described coupling procedure is employed to couple the hexadecapeptide with a pentapeptide, $N_\alpha$-benzyloxycarbonyl-im-benzylhistidyl-leucyl-valyl-glutamyl-($\gamma$-t-butyl ester)-alanine hydrazide. The benzyloxycarbonyl blocking group is removed from the terminal histidyl residue of the resulting heneicosapeptide by treatment with hydrobromic acid, followed by treatment with base which hydrolyzes the terminal alanine methyl ester to the carboxylic acid. The heneicosapeptide thus obtained is coupled via the nitrous acid procedure described hereinabove with a nonapeptide, $N_\alpha$-benzyloxycarbonyl-phenylalanyl-valyl-asparagylglutamyl-benzylhistidyl-leucyl-S-benzylcysteyl-glycyl-serine hydrazide. The resulting tricontapeptide is purified chromatographically as described hereinabove and deblocked by treatment with sodium in liquid ammonia to give the insulin B chain.

It will be apparent to those skilled in the art that various modifications of the procedures described hereinbefore are possible without departing from the spirit and scope of the invention.

What is claimed is:

1. A composition which comprises a resin crosslinked with from about 0.5 to about 3 percent by weight divinylbenzene and swollen to an equilibrium state by a solvent which is essentially N-methyl-2-pyrrolidone, which resin is polystyrene or a polystyrene substituted with an anchoring group capable of reacting with the amino or carboxy terminus of an amino acid or peptide to give a covalent bond.

2. The composition of claim 1, wherein said resin is crosslinked with from about 0.5 to about 2 percent by weight divinylbenzene.

3. The composition of claim 1, wherein said N-methyl-2-pyrrolidone contains up to about 5 percent by volume of a cosolvent which swells said resin to a degree which is about equal to or greater than the degree of swelling of said resin which results from said N-methyl-2-pyrrolidone.

4. The composition of claim 3, wherein said cosolvent is chloroform.

5. The composition of claim 1, wherein said resin is polystyrene.

6. The composition of claim 1, wherein said resin is a polystyrene substituted with an anchoring group.

7. The composition of claim 6, wherein the anchoring group is chloromethyl.

* * * * *